US008399020B2

(12) United States Patent
Driessen et al.

(10) Patent No.: US 8,399,020 B2
(45) Date of Patent: Mar. 19, 2013

(54) SHAPED PLANT GROWTH NUTRIENT PRODUCTS AND PROCESSES FOR THE PRODUCTION THEREOF

(75) Inventors: Danny Andreas Maria Driessen, Stein (NL); Michael Gustaaf Eltink, Sittard (NL); Gerardus Jacobus Joseph Out, Sittard (NL); Johannes Gijsbertus Antonius Terlingen, Landgraaf (NL); Andreas Lerschmacher, Dusseldorf (DE); Peter Kuhlmann, Wulfrath (DE)

(73) Assignee: Everris International B.V., Heerlen (NL)

( * ) Notice: Subject to any disclaimer, the term of this patent is extended or adjusted under 35 U.S.C. 154(b) by 0 days.

(21) Appl. No.: 11/247,067

(22) Filed: Oct. 11, 2005

(65) Prior Publication Data
US 2006/0089259 A1 Apr. 27, 2006

Related U.S. Application Data

(60) Provisional application No. 60/617,995, filed on Oct. 12, 2004.

(51) Int. Cl.
*A61K 9/14* (2006.01)
*A61K 9/16* (2006.01)

(52) U.S. Cl. ........................................ 424/489; 424/490
(58) Field of Classification Search .................. 504/101; 71/64.13, 64.03
See application file for complete search history.

(56) References Cited

U.S. PATENT DOCUMENTS

| | | | |
|---|---|---|---|
| 3,223,518 A | 12/1965 | Hansen | |
| 3,472,644 A * | 10/1969 | Woodside et al. | 71/1 |
| 4,011,061 A | 3/1977 | Forseen et al. | |
| 4,019,890 A | 4/1977 | Fujita et al. | |
| 4,045,204 A | 8/1977 | Matsunaga et al. | |
| 4,055,974 A | 11/1977 | Jackson | |
| 4,474,595 A * | 10/1984 | Lawhon et al. | 71/28 |
| 4,560,400 A | 12/1985 | Allan et al. | |
| 4,657,576 A | 4/1987 | Lambie | |
| 4,752,317 A | 6/1988 | Detroit | |
| 4,880,455 A | 11/1989 | Blank | |
| 5,219,465 A | 6/1993 | Goertz et al. | |
| 5,405,426 A | 4/1995 | Timmons et al. | |
| 5,466,274 A | 11/1995 | Hudson et al. | |
| 5,554,577 A * | 9/1996 | Kempf et al. | 504/358 |
| 5,652,196 A | 7/1997 | Luthra et al. | |
| 5,993,505 A * | 11/1999 | Tijsma et al. | 71/64.11 |
| 6,139,597 A | 10/2000 | Tijsma et al. | |
| 6,656,882 B2 * | 12/2003 | Tijsma et al. | 504/101 |
| 6,787,234 B2 | 9/2004 | Tijsma et al. | |
| 6,987,082 B2 * | 1/2006 | Tijsma et al. | 504/101 |
| 2002/0011087 A1 | 1/2002 | Neyman et al. | |
| 2002/0011887 A1 | 1/2002 | Stave | |
| 2002/0045727 A1 | 4/2002 | Weyer et al. | |
| 2003/0154755 A1 | 8/2003 | Horchler et al. | |
| 2004/0009878 A1 | 1/2004 | Lynch | |
| 2005/0175577 A1 * | 8/2005 | Jenkins et al. | 424/76.1 |
| 2007/0072775 A1 * | 3/2007 | van Boxtel-Verhoeven et al. | 504/367 |

FOREIGN PATENT DOCUMENTS

| | | | |
|---|---|---|---|
| DE | 2021259 | * | 5/1978 |
| EP | 0380193 | | 1/1990 |
| FR | 2 301 497 | | 2/1976 |
| JP | 49-005754 | | 1/1974 |
| JP | 57-129894 | * | 8/1982 |
| JP | 60206879 | * | 10/1985 |
| JP | 49005754 | * | 4/1986 |
| JP | 61-247678 | * | 11/1986 |
| JP | 251397 | * | 10/1987 |
| JP | 01-093487 | | 4/1989 |
| JP | 08090149 | * | 4/1996 |
| JP | 10152387 | * | 11/1998 |
| JP | 536811 | * | 12/2007 |
| WO | WO 84/03503 | | 9/1984 |
| WO | WO 93/19023 | | 9/1993 |
| WO | WO 96/18591 | | 6/1996 |
| WO | WO 96/27288 | | 9/1996 |
| WO | WO-9741726 | * | 11/1997 |
| WO | WO 99/36168 | | 7/1999 |

OTHER PUBLICATIONS

Japanese Patent Office Notice of Reasons for Rejection in Japanese Application 2007-536811, dated Dec. 15, 2011.
Nakayama, "Fertiliser for Horticultural Application—Comprises Mixing Fertiliser Component with Water-Soluble Thermoplastic Resin and Plasticiser and Moulding Mixt. to Form," WPI/Thompson vol. 1989, No. 21 (1989).
Supplementary European Search Report for European Application No. EP 05 80 4384, mailed Aug. 31, 2011.
Office Action Response and Argument to Japanese Patent Office Notice of Reasons for Rejection in Japanese Application 2007-536811, dated Apr. 16, 2012.

* cited by examiner

*Primary Examiner* — Alton Pryor
(74) *Attorney, Agent, or Firm* — Hunton & Williams LLP

(57) ABSTRACT

Shaped plant growth nutrient products such as fertilizer products are provided as well as processes for producing and using such shaped plant growth products. The products comprise active plant growth ingredients mixed with a biodegradable, water dispersible, water soluble, thermoplastic polymeric binding agent. Preferably, the shaped products are in tablet form and the active plant growth ingredient comprises a fertilizer.

21 Claims, No Drawings

SHAPED PLANT GROWTH NUTRIENT PRODUCTS AND PROCESSES FOR THE PRODUCTION THEREOF

BACKGROUND OF THE INVENTION

1. Field of the Invention

The present invention relates generally to shaped plant growth nutrient products and to processes for producing such shaped plant growth products. More particularly, it relates to products prepared by mixing active plant growth ingredients such as coated and uncoated plant nutrients with a biodegradable, water dispersible, water soluble, thermoplastic polymeric binding agent to produce shaped plant growth nutrient products such as fertilizer products, preferably in tablet form. The invention further relates to processes for producing such shaped plant growth nutrient products as well as to methods for using such shaped products for treating plants and vegetation.

2. Description of Related Art

Shaped plant nutrient formulations in tablet, spike or other forms have been known heretofore for targeting the application of plant growth nutrients to plants in a defined area. Exemplary of such prior products are those described in published European Patent Application EP0380193 A2. That published application describes the preparation and application of molded bodies containing nutrients, active ingredients, plant treatment agents and auxiliaries. The molded bodies are made from particles bound together by substance bridges consisting of thermally or chemically hardened binding agents including epoxy resins and polyurethane resins. It should be noted that both polyurethane and the epoxy resins are crosslinked resins and, therefore, are insoluble in water or other solvents.

U.S. Pat. No. 4,055,974 describes fertilizer tablets prepared from particles of fertilizer source materials which are bonded together with water insoluble, water swellable, hydrophilic polymeric gels by a cured water insoluble thermoset resinous binder such as urea formaldehyde. The resulting tablets are described as being adapted to absorb water and disintegrate. However, as with the tablets described in European Patent Application EP0380193 A2, the water insoluble binders cause undesirable environmental results due to their slow degradation properties when applied to the plant soil. Furthermore, since the binder employed to produce the tablets in accordance with U.S. Pat. No. 4,055,974 is a thermoset resin, efficient and cost effective melt processing techniques to produce the tablets cannot be performed and the cost and efficiency in producing the tablets is adversely impacted.

U.S. Pat. No. 4,011,061 describes the production of fertilizer tablets employing organic, film-forming preferably thermoplastic resin binders which are water insoluble and present environmental problems while U.S. Pat. No. 4,752,317 describes the production of a highly compacted product sold as a spike or a tablet. The product is prepared by mixing fertilizer ingredients with a water dispersible hydrolyzed lignosulfonate-acrylonitrile graft copolymer binder which is water soluble but not thermoplastic and presents problems relating to the techniques required to produce the product.

Several commercial products are presently on the market which comprise tablets prepared from fertilizer granules and polyurethane binders. However, these tablets all exhibit environmental disadvantages attributable to the durability of the polyurethane binder systems employed. For example, when so-called controlled release fertilizer (CRF) granules in such a tablet fully release their nutrients to a treated plant, the tablet retains its initial shape as if the fertilizer tablet has not been active. Furthermore, the production of these prior plant growth nutrient tablets has resulted in various problems such as those encountered concerning the build-up of cured resin residue on the tablet forming mold which is difficult to remove.

Another example of current products being marketed is presented by tablets prepared from coated fertilizer granules and a water swellable, thermosetting polymeric binder system. However, as a result of its inability to melt, in production the polymeric binder must be applied from the constituent monomers or prepolymers in an emulsion or solution, which requires an additional drying stage in the tablet production process. The ultimate thermoset resin is formed upon aging.

Generally, the active plant growth/nutrient ingredients employed in the production of fertilizer tablets are coated fertilizers which, in use, have a number of advantages over uncoated fertilizers and are known to be very effective sources to provide controlled release of nutrients for the feeding of plants. The nutrients are released through the fertilizer's coating at controlled rates and in this way the nutritional need of the plants can be exactly matched. By selection of a suitable coating thickness or coating composition, an appropriate fertilizer longevity can be attained. By doing so, one application of these CRF's can provide the necessary nutrients for a plant that would take multiple applications of soluble fertilizer, without the risk of overfeeding of plants or leaching of fertilizer minerals to the environment.

In the CRF's, the fertilizer may release out of the coatings in various ways such as via: 1) imperfections in the coating, 2) pores in the coating or 3) osmotic pressure. It has been recognized heretofore that the latter two mechanisms offer important benefits over the first in regard to consistency of release rates.

An example of coated fertilizers which exhibit fertilizer release via coating imperfections are the sulfur coated fertilizers with a polymeric topcoat, such as disclosed in U.S. Pat. Nos. 5,219,465; 5,405,426 and 5,466,274. The major advantage of the sulfur coated fertilizers with a polymeric topcoat is their relatively low cost.

Examples of coated fertilizers which show fertilizer release through pores in the coating are presented by the polyolefin coated fertilizers such as disclosed in U.S. Pat. No. 4,019,890.

Fertilizer release by water vapor permeation through the coating and subsequent build-up of osmotic pressure is exhibited by fertilizers with solvent applied thermosetting resin coatings. Examples of solvent applied thermosetting resin coated fertilizers which are currently in use are disclosed in U.S. Pat. Nos. 3,223,518; 4,657,576; 4,880,455, 5,652,196; 5,993,505 and 6,139,597.

SUMMARY OF THE INVENTION

In accordance with the present invention, we have found that problems encountered in regard to the composition, formation and use of prior shaped plant growth nutrient products such as those in tablet form can be overcome simply and practically by bonding a predetermined amount of one or more types of coated granules having the same or different longevity and, optionally, other materials such as uncoated fertilizer granules, water absorbent gels, herbicides, insecticides, fungicides, pheromones, biostimulants, growth regulators, animal repellents, insect repellents and the like together into a tablet of predetermined dimension employing a specific suitable binding system agent. The shaped form (eg, tablet) dimensions can be designed so as to meet the nutritional need of the plants to which fertilization is applied.

Materials suitable for use in the production of the shaped products (eg, tablets) of the present invention are biodegradable, water dispersible, water soluble, thermoplastic polymers which serve as binding agents and, in some cases, as wetting agents.

In comparison to prior shaped products and production techniques therefor which employ crosslinked resin binders or binders requiring application from an emulsion or solution, the present thermoplastic binding agents enable simple and efficient tablet production and in comparison to prior products and production techniques which make use of crosslinked, water insoluble binders, the present water soluble binding agents enable production of environmentally advantageous shaped products such as those in tablet form.

DETAILED DESCRIPTION OF THE INVENTION

Plant growth nutrient tablets in accordance with the present invention may be prepared utilizing active plant growth ingredients including coated and uncoated plant nutrient granules such as fertilizer granules, biostimulants, growth regulators, plant treating agents, fertilizer additive ingredients and the like and mixtures thereof.

Preferably, the plant growth nutrient tablets are prepared utilizing homogeneous or heterogeneous coated fertilizer granules. When homogeneous or single component granules are employed, the granules have a diameter ranging from about 0.1 to about 10 mm, preferably, between about 0.5-5 mm. When heterogeneous or multiple component granules are employed, the granules may be of varying composition, diameter (about 0.1 to about 10 mm), coating type, coating thickness (longevity) and the like. Preferably, when heterogeneous granules are employed, small dimension granules (about 0.2-1.5 mm) are mixed with larger dimension granules (about 2-5 mm) to produce the tablets.

The granules may have one or more coatings applied thereon with coating thicknesses varying between about 0.1 and 150 micrometers, preferably between about 1 and 110 micrometers and longevities ranging between about 1 week to 24 months, preferably between about 3 weeks and 18 months. The fertilizer granules for use herein may include such materials as Nitrogen (N), Phosphorus (P) and/or Potassium (K) or any of a variety of different NPK compositions which may or may not contain Magnesium, Calcium and/or various amounts of various trace elements such as Boron, Iron, Cobalt, Copper, Manganese, Molybdenum, Zinc.

In a preferred embodiment, the granules are preheated to a temperature in the range of about 50-100° C. and then mixed with about 0.1-40 wt %, preferably about 1-25 wt % of a suitable binding agent which has previously been heated to form a melt. To this mixture, optionally, one or more other components may be added such as water-absorbent gels, nitrification inhibitors, urease inhibitors, herbicides, insecticides, fungicides, pheromones, animal repellents, insect repellents and the like and mixtures thereof.

For the binding agent, a biodegradable, water dispersible, water soluble, thermoplastic polymeric material is used. We have found that polymers from the group comprising C1-C4-polyalkylene oxide homopolymers, C1-C4-polyalkylene oxide block copolymers- and terpolymers and polyolefin-C1-C4-polyalkylene oxide block copolymers and mixtures thereof exhibit unexpectedly advantageous characteristics in regard to crystallization behavior, adhesive properties, water solubility, biodegradability and, in some cases, wetting properties.

Suitable examples of such polymers are polyethylene oxide homopolymers, polyethylene oxide-block-polypropylene oxide copolymers, polyethylene oxide-block-polypropylene oxide-block-polyethylene oxide terpolymers, polypropylene oxide-block-polyethylene oxide-block-polypropylene oxide terpolymers, polyethylene-block-polyethylene oxide copolymers, polyethylene-block-polypropylene oxide copolymers, polypropylene-block-polyethylene oxide copolymers and polypropylene-block-polypropylene oxide copolymers and the like and mixtures thereof.

Preferably, the melt temperature of the binding agent should range between about 50° C. and about 160° C., preferably between about 50° C. and about 100° C.

The melt temperature, melt viscosity and mechanical behavior of the polymeric binding agent is a function of the chemical composition and the molecular weight of the polymer and in case of block copolymers additionally of the block length of the polyethyleneoxide-, polyethylene- or polypropylene-segment. In accordance with the present invention, the physical and chemical characteristics of the polymer may be selected so that the melt temperature and melt viscosity of the polymer are low enough to allow safe and efficient coating of the granules with the binding agent but are high enough to enable sufficient mechanical strength of the resulting tablets.

The block copolymers have the additional advantage over the homopolymers of exhibiting wetting properties, which enhance the rate of water absorption in the soil. The water solubility and wettability of the block copolymers are dependent on the relative amount of the water soluble segments, which is chosen such that the mechanical stability of the tablets is not influenced.

In a preferred embodiment, the plant growth granules and any ancillary ingredients are preheated to a temperature in a range of about of 50-100° C. and then mixed with about 0.1-40 wt % of the binding agent which has previously been heated to form a melt. The resulting mixture is introduced into a shaping mold and the mixture is cooled in the mold to form the shaped product.

The following examples further illustrate details of the products and processes of the present invention. While the invention is described with preferred embodiments, it is to be understood that variations and modifications thereof may be resorted to as will be apparent to those skilled in the art. Such variations and modifications are to be considered within the purview and the scope of the claims appended hereto.

EXAMPLE 1

Fertilizer tablets in accordance with the present invention were prepared by mixing 83 wt % preheated Osmocote® Exact® Standard 3-4 Month fertilizer granules with average diameter of 3.1 mm, sold by The Scotts Company, and 9 wt % preheated Osmocote® Exact® Mini 3-4 Month with average diameter of 1.5 mm, sold by The Scotts Company, with 8 wt % polyethylene oxide having a molecular weight of 8000 g/mole at 90° C. After thorough mixing, the mixture was spread out over a tablet mold, after which the excess of the granulate-binder mixture was scraped off. The mold was allowed to cool down to ambient temperature and the tablets were removed. Drop tests showed that the average weight loss was small. In water, the tablets showed rapid disintegration into separate granules.

EXAMPLE 2

A control sample product in accordance with the prior art was prepared by combining and mixing 375 g Osmocote® Exact® Standard 3-4 Month fertilizer granules, sold by The Scotts Company, having an average diameter of 3.1 mm and with NPK 16+11+11; 5 g Askofen 3289 Part A polyol formulation comprising 4-hydroxy-4-methylpentane-2-on, sold by Ashland-Sudchemie-Kernfest GMBH; and 5 g Askofen 0281 Part B comprising diphenylmethane-4,4'-diisocyanate, isomers and homologs, sold by Ashland-Sudchemie-Kernfest GMBH at room temperature. The resulting mixture was quickly spread out over a silicone rubber tablet mold and the excess of the mixture was scraped off. After 15-20 minutes curing, the resulting tablets were removed from the mold.

Experience has demonstrated that the production of these prior products utilizing polyurethane binder technology has presented various problems that are overcome by the present invention. For example, employing the prior techniques, all the equipment had to be cleaned quickly and regularly, because the resin was very difficult to remove after curing. Expensive silicone rubber molds were required to produce the tablets because tablet removal from metal molds was found to be difficult as a result of the strong adhesion of the tablets to the mold surface. In practice, it was further found that the molds should be renewed every 10 weeks due to resin build-up and damaging of the molds. Still further, once Askofen 3289 Part A and Askofen 0281 Part B were mixed, the resulting mixture had to be applied rapidly because the pot life was very limited. Nevertheless, it was found that a significant amount of spill material was produced which could not be used a second time.

In comparison, it has been found that the problems encountered in producing the tablet products of the prior art are effectively and cost efficiently resolved employing the formulations and processes of the present invention as exemplified herein by Example 1

EXAMPLE 3

In a further comparative example, three separate commercially available fertilizer tablet samples which utilize thermoset binders were compared with a sample of the fertilizer tablets of the present invention employing a biodegradable, water dispersible, water soluble, thermoplastic polymeric binding agent and the results of the testing performed on the fertilizer tablet samples in terms of water solubility, tablet disintegation and mechanical stability were tabulated (see Table 1 hereinbelow).

For purposes of the comparative testing, a 5.4 gram Osmocote® Plus fertilizer tablet sold by The Scotts Company; a 7.6 gram Basacote® Plus Tabs 6 Month fertilizer tablet sold by Compo GMBH & Co. KG. and a 6.0 gram Pokon Season Comfort fertilizer tablet sold by Pokon & Chrysal BV were employed as examples of prior fertilizer tablets produced utilizing thermoset binders. As an example of a fertilizer tablet in accordance with the present invention, a 5.3 g fertilizer tablet sample was prepared in accordance with the procedure set forth in Example 1 utilizing the same biodegradable, water dispersible, water soluble, thermoplastic polymeric binding agent as employed in Example 1.

The sample fertilizer tablets were placed in glass beakers filled with 200 ml water at 21° C. After 19 minutes in the water, the tablet produced according to the present invention was found to disperse into separate granules. The Pokon Season Comfort tablet and the somewhat larger Basacote Plus Tabs tablet exhibited swelling but no dissolution of the binder. After 5 hours, the Pokon and Basacote tablets fell apart into separate granules in a soft crosslinked mass. The Osmocote Plus tablet retained its initial shape and remained rigid.

The results of the comparative testing performed on the sample tablets were as follows:

| Binder Type | Tablet Type (Binder Employed) | Water Soluble Binder at (21° C.) | Tablet Desintegration - time in water at 21° C.[a] | Mechanical Stability[b] |
| --- | --- | --- | --- | --- |
| Thermoplastic | Present invention (5.3 g) | Yes | 19 Minutes | 3.4% |
| Thermoset | Osmocote Plus (5.2 g) | No | Indefinite | 1.1% |
| Thermoset | Pokon Season Comfort (5.3 g) | Water swellable | 5 hours | 0.4% |
| Thermoset | Basacote Tabs 6M (7.6 g) | Water swellable | 5 hours | 0.4% |

[a] Time that it takes before the tablet falls apart into separate granules
[b] Average percent weight loss of 10 tablets in a 2 meter drop test at 21° C.

EXAMPLE 4

In another comparative example, separate samples of a 5.4 gram Osmocote® Plus fertilizer tablet, a 7.6 gram Basacote® Plus Tabs 6 Month fertilizer tablet; and a 6.0 gram Pokon Season Comfort fertilizer tablet and a 5.2 g fertilizer tablet of the present invention prepared in accordance with the procedure set forth in Example 1 were placed in separate glass beakers and placed in an oven at 100® C. for a period of 30 minutes. Thereafter, the tablet produced according to the present invention was found to disintegrate readily into separate coated granules upon touching due to melting of the binding agent. The Osmocote® Plus tablet, the Basacote Plus tablet and the Pokon Season Comfort tablet were found to retain their initial shape and remained rigid even upon slight pressure exertion and temperature increase to 150° C., demonstrating that the binding agent used in each of these tablets was a thermoset polymer rather than a thermoplastic polymer as employed in the present invention.

EXAMPLE 5

92 wt % samples of preheated Osmocote Exact Standard 3-4 Month fertilizer granules with average diameter of 3.1 mm and with NPK 16+11+11 were mixed with 8 wt % polyethylene oxide having molecular weights of 6000 g/mole, 8000 g/mole and 20,000 g/mole, respectively, at 90° C. After thorough mixing, the sample mixtures were spread out over separate tablet molds, after which the excess of each mixture was scraped off. The mold was allowed to cool down to ambient temperature and the tablets were removed from the mold. When placed in water, each of the resulting sample tablets showed rapid disintegration into separate granules. Drop tests showed that the average weight loss was acceptable for the polyethylene oxide with molecular weight of 6000 and 8000 g/mole but not for the polyethyleneoxide with 20,000 g/mole, due to uneven distribution of the high molecular weight polyethyleneoxide binding agent on the granules. This demonstrates that selection of polymer properties must be made carefully. Too high molecular weight results in too high viscosity and, thereby, adverse mixing behavior and loss of mechanical stability of the tablets. Too low molecular weight, however, may result in stickiness due to low melting point and also loss of mechanical stability of the tablets. Accordingly, it appears that only a narrow band of molecular weights is suitable for the production of stable tablets.

EXAMPLE 6

92 wt % preheated Osmocote Exact Standard 5-6 Month fertilizer granules was mixed with 8 wt % Synperonic™ PEF 108 polyethyleneoxide-block-polypropyleneoxide-block-polyethyleneoxide terpolymer, sold by Uniqema, having a molecular weight of 14,000 g/mole at a temperature of 90° C. After thorough mixing, the mixture was spread out over a tablet mold, after which the excess of the granulate-binder mixture was scraped off. The mold was allowed to cool down to ambient temperature and the tablets were removed. In water, disintegration of the resulting tablets into separate granules occurred rapidly.

EXAMPLE 7

92 wt % preheated Osmocote Exact Standard 3-4 Month fertilizer granules were mixed with 8 wt % polyethylene-block-polyethyleneoxide copolymer having a molecular weight of 2250 g/mole at a temperature of 90° C. After thorough mixing, the mixture was spread out over a tablet mold, after which the excess of the granulate-binder mixture was scraped off. The mold was allowed to cool down to ambient temperature and the tablets were removed. In water, disintegration of the resulting tablets into separate granules occurred rapidly.

EXAMPLE 8

60 wt % preheated Osmocote Exact 3-4 Month fertilizer granules and 20 wt % Luquasorb® 1161 sodium polyacrylate water absorbent gel sold by BASF were mixed with 20% polyethylene oxide having a molecular weight of 8000 g/mole at 90° C. After thorough mixing, the mixture was spread out over a tablet mold after which the excess of the mixture was scraped off. The mold was allowed to cool down and the resulting tablets were removed. The tablets dispersed quickly in water and the added Luquasorb water absorbent gel showed satisfactory swell behavior. Drop tests showed acceptable tablet stability.

EXAMPLE 9

92 wt % preheated Osmocote Exact Standard 5-6 Month fertilizer granules were mixed with 8 wt % of a mixture of 87 wt % polyethylene oxide having a molecular weight of 8000 g/mole and 13 wt % aluminium tris-O-ethylphosphonate (fosetyl-aluminium) fungicide at 90° C. After thorough mixing, the mixture was spread out over a tablet mold, after which the excess of the mixture was scraped off. The mold was allowed to cool down to ambient temperature and the resulting tablets were removed from the mold.

EXAMPLE 10

92 wt % preheated uncoated fertilizer granules (NPK 17+10+13+trace elements) were mixed with 8 wt % polyethylene oxide having a molecular weight of 8000 g/mole. After thorough mixing, the mixture was spread out over a tablet mold, after which the excess of the mixture was scraped off. The mold was allowed to cool down to ambient temperature and the resulting tablets were removed from the mold.

EXAMPLE 11

92 wt % preheated Osmocote® Start (NPK 12+11+17+2 MgO+trace elements) fertilizer granules sold by The Scotts Company, with an average diameter of 1.6 mm, were mixed with 8 wt % polyethylene oxide having a molecular weight of 8000 g/mole at 90° C. After thorough mixing, the mixture was spread out over a tablet mold, after which the excess of the mixture was scraped off. The mold was allowed to cool down to ambient temperature and the resulting tablets were removed from the mold.

EXAMPLE 12

92 wt % preheated sulfur coated urea fertilizer granules, containing 11 wt % sulfur coating, were mixed with 8 wt % polyethylene oxide having a molecular weight of 8000 g/mole at 90° C. After thorough mixing, the mixture was spread out over a tablet mold, after which the excess of the mixture was scraped off. The mold was allowed to cool down to ambient temperature and the resulting tablets were removed from the mold.

EXAMPLE 13

92 wt % preheated Osmoform® (NPK 19+5+13+2MgO+ trace elements) fertilizer prills sold by The Scotts Company were mixed with 8 wt % polyethylene oxide having a molecular weight of 8000 g/mole at 90° C. After thorough mixing, the mixture was spread out over a tablet mold, after which the excess of the mixture was scraped off. The mold was allowed to cool down to ambient temperature and the resulting tablets were removed from the mold.

EXAMPLE 14

92 wt % preheated Basacote Plus 12 Month (NPK 15+8+ 12+2MgO+trace elements) fertilizer granules were mixed with 8 wt % polyethylene oxide having a molecular weight of 8000 g/mole at 75° C. After thorough mixing, the mixture was spread out over a tablet mold, after which the excess of the mixture was scraped off. The mold was allowed to cool down to ambient temperature and the resulting tablets were removed from the mold.

EXAMPLE 15

92 wt % preheated Sinclair Sincrocell 12 (NPK 14+8+13+ 2MgO+trace elements) fertilizer granules sold by William Sinclair Horticultural Ltd were mixed with 8 wt % polyethylene oxide having a molecular weight of 8000 g/mole at 90° C. After thorough mixing, the mixture was spread out over a tablet mold, after which the excess of the mixture was scraped off. The mold was allowed to cool down to ambient temperature and the resulting tablets were removed from the mold.

EXAMPLE 16

92 wt % preheated Nutricote® controlled release fertilizer (CRF) 100 day (NPK 13+13+13+2MgO+trace elements) granules sold by Chisso-Asahi Fertilizer Co., Ltd. were mixed with 8 wt % polyethylene oxide having a molecular weight of 8000 g/mole at 90° C. After thorough mixing, the mixture was spread out over a tablet mold, after which the excess of the mixture was scraped off. The mold was allowed to cool down to ambient temperature and the resulting tablets were removed from the mold.

EXAMPLE 17

92 wt % preheated Multicote® 4 (NPK 15+7+15+2MgO+ trace elements) controlled release fertilizer granules sold by Haifa Chemicals Ltd. were mixed with 8 wt % polyethylene oxide having a molecular weight of 8000 g/mole at 90° C. After thorough mixing, the mixture was spread out over a tablet mold, after which the excess of the mixture was scraped off. The mold was allowed to cool down to ambient temperature and the resulting tablets were removed from the mold.

In a further embodiment of the present invention, dosing systems are provided for granules or powders which can be used in a variety of water based systems or wet surroundings where rapid availability of a solid substrate is desired. For example, tablets of this invention can be formulated to supply disinfecting chemicals, as for swimming pool applications, to replace standard chemical solution applications. Also, tablets of this invention can be formulated for introduction into dipping baths, such as those employed in the paint industry, to add chemicals such as fungicides and biocides into the baths during the long duration of the baths. Still further, tablets can be formulated with water soluble binders to provide dosing systems for introducing pigments or tinting materials into paints as a replacement for high viscosity pastes which have been employed heretofore.

Although the invention has been described in its preferred forms with a certain degree of particularity, it is to be understood that the present disclosure has been made by way of example only. Numerous changes in the details of the compositions and ingredients therein as well as the methods of preparation will be apparent without departing from the spirit and scope of the invention, as defined in the appended claims.

The invention claimed is:
1. A product comprising:
    coated active plant growth nutrient granules; and
    a biodegradable, water dispersible, water soluble, thermoplastic polymeric binding agent comprising C1-C4-polyalkylene oxide with a melt temperature in the range of about 50° C. to about 160° C.;
    wherein the coated plant growth nutrient granules are held together by the binding agent in a mechanically stable, shaped controlled release plant growth nutrient product, said shaped controlled release plant growth nutrient product is dispersed rapidly into separate granules after contact with water.
2. The product of claim 1, wherein the C1-C4-polyalkylene oxide is a C1-C4-homopolymer, C1-C4-polyalkylene oxide block co-polymer or terpolymer, or polyolefin-C1-C4-polyalkylene oxide block co-polymer.
3. The product of claim 1, wherein the active plant growth nutrient granules have a diameters ranging from about 0.1 to about 10 millimeters.
4. The product of claim 3, wherein the active plant growth nutrient granules have a diameters ranging from between about 0.5 to 5 millimeters.
5. The product of claim 4, wherein the plurality of coated active plant growth nutrient granules have diameters ranging from about 2 to 5 millimeters.
6. The product of claim 3, comprising a second plurality of active plant growth nutrient granules having diameters ranging from about 0.2 to 1.5 millimeters.
7. The product of claim 1, wherein the shaped controlled release plant growth nutrient product comprises about 0.1 to 40 weight percent binding agent.
8. The product of claim 7, wherein the shaped controlled release plant growth nutrient product comprises between about 1 to 25 weight percent binding agent.
9. The product of claim 1, wherein the binding agent includes polyethylene oxide homopolymers, polyethylene oxide-block-polypropylene oxide copolymers, polyethylene oxide-block-polypropylene oxide-block-polyethylene oxide terpolymers, polypropylene oxide-block-polyethylene oxide-block-polypropylene oxide terpolymers, polyethylene-block-polyethylene oxide copolymers, polyethylene-block-polypropylene oxide copolymers, polypropylene-block-polyethylene oxide copolymers, polypropylene-block-polypropylene oxide copolymers or mixtures thereof.
10. The product of claim 1, wherein the binding agent has a melt temperature in the range of about 50° C. to 100° C.
11. The product of claim 1, wherein the active plant growth nutrient granules are plant nutrients, biostimulants, growth regulators, plant treating agents, fertilizer additive ingredients, or mixtures thereof.
12. The product of claim 1, wherein at least one other component is mixed with the active plant growth nutrient granules and the binding agent, the other component including water-absorbent gels, nitrification inhibitors, urease inhibitors, herbicides, insecticides, fungicides, pheromones, animal repellents, insect repellents or mixtures thereof.
13. A process for producing shaped plant growth nutrient products comprising:
    providing coated granules of an active plant growth nutrient ingredient;
    preheating the granules to a temperature in the range of about 50-100 ° C.;
    mixing said granules with a biodegradable, water dispersible, water soluble, thermoplastic polymeric binding agent comprising C1-C4-polyalkylene oxide with a melt temperature in the range of about 50° C. to about 160° C. which has been heated to form a melt, wherein the mixture comprises about 0.1 to 40 weight percent binding agent; and
    introducing the mixture into a mold and cooling the mixture in the mold to form the shaped plant growth nutrient product, wherein the coated plant growth nutrient granules are held together by the binding agent in a mechanically stable, shaped controlled release plant growth nutrient product, said shaped controlled release plant growth nutrient product is dispersed rapidly into separate granules after contact with water.
14. The process of claim 13, wherein the mixture comprises about 1 to 25 weight percent binding agent.
15. The process of claim 13, wherein the product is shaped in tablet form.
16. The process of claim 13, wherein the granules are plant nutrients, biostimulants, growth regulators, plant treating agents, fertilizer additive ingredients or mixtures thereof.
17. The process of claim 13, wherein the granules are coated fertilizer granules.
18. The process of claim 13, wherein at least one other component is mixed with the active plant growth ingredient and the binding agent, the other component includes coated fertilizer granules, uncoated fertilizer granules, water-absorbent gels, nitrification inhibitors, urease inhibitors, herbi- cides, insecticides, fungicides, pheromones, animal repellents, insect repellents or mixtures thereof.

19. The process of claim 13, wherein the binding agent includes C1-C4-polyalkylene oxide homopolymers, C1-C4-polyalkylene oxide block co-polymers and terpolymers, polyolefin-C1-C4-polyalkylene oxide block copolymers or mixtures thereof.

20. The product of claim 13, wherein the binding agent includes polyethylene oxide homopolymers, polyethylene oxide-block-polypropylene oxide copolymers, polyethylene oxide-block-polypropylene oxide-block-polyethylene oxide terpolymers, polypropylene oxide-block-polyethylene oxide-block-polypropylene oxide terpolymers, polyethylene-block-polyethylene oxide copolymers, polyethylene-block-polypropylene oxide copolymers, polypropylene-block-polyethylene oxide copolymers, polypropylene-block-polypropylene oxide copolymers or mixtures thereof.

21. The process of claim 13, wherein the C1-C4-polyalkylene oxide is a C1-C4-homopolymer, C1-C4-polyalkylene oxide block co-polymer or terpolymer, or polyolefin -C1-C4-polyalkylene oxide block co-polymer.

* * * * *